United States Patent
Sattler et al.

(10) Patent No.: US 9,031,695 B2
(45) Date of Patent: May 12, 2015

(54) MEDICAL DIAGNOSIS AND/OR INTERVENTION DEVICE

(75) Inventors: Stefan Sattler, Forchheim (DE); Reiner Staab, Baiersdorf (DE); Susanne Staab, legal representative, Baiersdorf (DE); Katharina Staab, legal representative, Aschaffenburg (DE); Silvia Rachor, legal representative, Goldbach (DE)

(73) Assignee: Siemens Aktiengesellschaft, München (DE)

( * ) Notice: Subject to any disclaimer, the term of this patent is extended or adjusted under 35 U.S.C. 154(b) by 1464 days.

(21) Appl. No.: 12/218,069

(22) Filed: Jul. 10, 2008

(65) Prior Publication Data
US 2009/0018701 A1    Jan. 15, 2009

(30) Foreign Application Priority Data
Jul. 12, 2007 (DE) .......................... 10 2007 032 538

(51) Int. Cl.
| | |
|---|---|
| G05B 19/406 | (2006.01) |
| A61B 6/10 | (2006.01) |
| A61B 6/00 | (2006.01) |
| A61B 19/00 | (2006.01) |

(52) U.S. Cl.
CPC . *A61B 6/102* (2013.01); *A61B 6/56* (2013.01); *A61B 19/2203* (2013.01); *A61B 19/26* (2013.01); *A61B 2019/5238* (2013.01)

(58) Field of Classification Search
CPC .......... A61B 6/102; A61B 19/26; A61B 6/56; A61B 19/5238; A61B 19/2203; B25J 19/0045; B25J 19/005; B25J 9/1666; B25J 9/1674; B25J 9/1676; B25J 9/1694
USPC ............ 318/568.11, 568.12, 568.16; 33/503; 606/130; 700/245, 250, 253, 254, 255, 700/258; 74/490.01, 490.02, 490.03, 74/490.07, 490.1, 490.11
See application file for complete search history.

(56) References Cited

U.S. PATENT DOCUMENTS

| | | | | |
|---|---|---|---|---|
| 4,969,170 | A | * | 11/1990 | Kikuchi et al. ................. 378/91 |
| 6,166,506 | A | * | 12/2000 | Pratt et al. ................. 318/568.12 |
| 6,278,210 | B1 | * | 8/2001 | Fatula et al. .................. 310/112 |
| 6,343,242 | B1 | * | 1/2002 | Nomura et al. ............... 700/245 |
| 2001/0008389 | A1 | * | 7/2001 | Serban et al. ................... 338/47 |
| 2001/0052735 | A1 | | 12/2001 | Sakamoto |
| 2002/0184751 | A1 | * | 12/2002 | Jin et al. ....................... 29/602.1 |
| 2003/0191603 | A1 | * | 10/2003 | Raab et al. .................... 702/150 |
| 2006/0149418 | A1 | * | 7/2006 | Anvari .......................... 700/245 |
| 2007/0137372 | A1 | * | 6/2007 | Devengenzo et al. ..... 74/490.01 |

FOREIGN PATENT DOCUMENTS

| | | |
|---|---|---|
| DE | 36 16 389 A1 | 11/1987 |
| DE | 3616389 A1 | 11/1987 |
| DE | 20116756 U1 | 1/2002 |
| DE | 20206108 U1 | 7/2002 |
| DE | 202 06 108 U 1 | 8/2002 |
| DE | 10 2004 042 489 A1 | 3/2006 |
| DE | 102004042489 A1 | 3/2006 |
| DE | 10 2005 049 106 A1 | 4/2007 |
| DE | 102005049106 A1 | 4/2007 |
| JP | 2001233598 A * | 8/2001 |

* cited by examiner

Primary Examiner — Stephen Holwerda

(57) ABSTRACT

On a medical diagnosis and/or intervention device having a movable component, collision sensors are to be arranged without the cabling outlay becoming too high. This is made possible by the collision sensors being capable of sending signals wirelessly. The voltage supply can also be provided wirelessly along a section by using e.g. a slip ring.

10 Claims, 1 Drawing Sheet

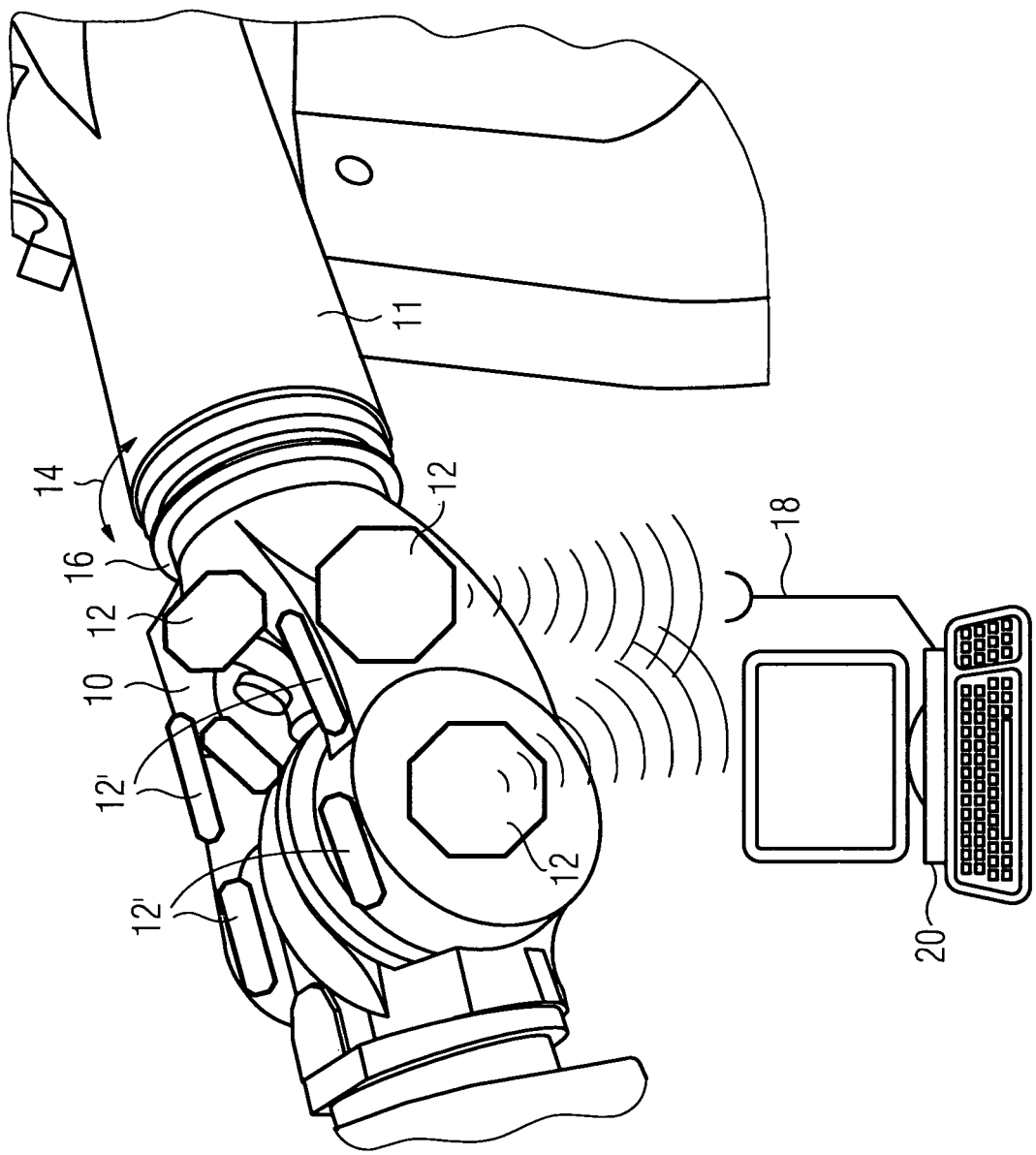

MEDICAL DIAGNOSIS AND/OR INTERVENTION DEVICE

CROSS REFERENCE TO RELATED APPLICATIONS

This application claims priority of German application No. 10 2007 032 538.1 filed Jul. 12, 2007, which is incorporated by reference herein in its entirety.

FIELD OF THE INVENTION

The invention relates to a medical diagnosis and/or intervention device.

BACKGROUND OF THE INVENTION

Medical diagnosis and/or intervention devices can perform increasingly complex linear and rotational movements. An example of such a device is an x-ray imaging device in which the latest developments provide a six-axis articulated robot that holds and moves an x-ray C-arm with x-ray radiation source and x-ray detector. Increasing the number of degrees of freedom in the movement of movable components of medical diagnosis and/or intervention devices heightens the risk of collisions in particular between the respective movable component and people or objects. It is known how to provide at least one apparatus at the respective movable component for recording a situation of an upcoming and/or ongoing collision of the component with an obstacle. This apparatus can comprise simple touch-sensitive sensors or also photosensors and lots more.

It is necessary to supply the apparatus with a voltage that is required for it to function. On the other hand a control apparatus of the medical diagnosis and/or intervention device must somehow be informed when a collision situation is recorded. Corresponding signals have previously been provided through cables.

The cabling outlay can disrupt the movement of the movable component. The more complex the movements are, the more desirable it is to provide a greater number of the aforementioned apparatuses for recording a collision situation. The number of cables to be used also increases accordingly. In the case of certain movable components the type of movement is not consistent with installing a cable. This applies in the first instance to any rotatable component, but especially for continuously rotatable components such as those represented by certain robotic hands. The movements of the movable component would have to be restricted through the controls in order to provide such cabling. As there is a tendency to refrain from interfering with the control of such movable components, apparatuses for recording a collision situation have not previously been inserted in continuously rotatable components.

SUMMARY OF THE INVENTION

The object of the invention is to enable a maximally widespread use of apparatuses for recording collision situations in medical diagnosis and/or intervention devices.

This object is achieved by a medical diagnosis and/or intervention device according to the claims.

According to the first aspect of the invention the apparatus for recording a situation of an upcoming and/or ongoing collision is designed to send and possibly also to receive wireless signals, with the signals being addressed to the control apparatus that controls the movement of the component. Cable is conserved, i.e. the cabling outlay is reduced, through the wireless communication of the apparatus for recording a collision situation with the respective control apparatus. As a result there will be a greater tendency to use one or more of the aforementioned apparatuses.

A voltage supply to the apparatus is preferably also enabled without there being provided a cable conductor for this purpose that leads away from the rest of the body of the device, opposite which the movable component moves, and toward the movable component. This means that no cables whatsoever are required, such that the cabling no longer gives rise to a quantitative limitation of the apparatuses for recording a collision situation. Owing to the fact that the need for cabling is entirely obviated, the use of apparatuses for recording a collision situation is also possible on those components for which the cabling had previously been obstructive. As mentioned above, these are the continuously rotatable components.

In the case of such continuously rotatable components the voltage supply can be provided for example via a slip ring on the rotatable component. The slip ring is arranged on the intersection between the rest of the body (opposite which the rotatable component rotates) and the rotatable component. The voltage supply can alternatively also be provided inductively upon rotation of the component. Known means must themselves accordingly be provided on the rest of the body and on the movable component, e.g. permanent magnets on the rest of the body and an induction coil on the movable component. As a third possibility it is proposed to arrange a dynamo on the side of (i.e. on or in) the movable component, said dynamo charging a battery upon rotation of the movable component, and this battery then supplies the apparatus for recording a collision situation with the required voltage.

All three embodiments can be advantageous. Retrofitting the device with a slip ring can be especially rapid; the inductive generation of a voltage can be especially energy-efficient; and in the case of the embodiment that uses a dynamo, components are only necessary on or in the movable component, rather than on the rest of the body of the device.

The second aspect of the present invention focuses on the idea of providing the slip ring. The slip ring also saves on cabling, with the voltage supply being the primary area of interest rather than the communication. Above and beyond the first aspect of the invention, in which the apparatus for recording a collision situation communicates wirelessly, there are preferred embodiments in the case of this second aspect. Indeed, communication may not in fact be necessary. This is the case in particular if the apparatus is designed to act on the direct voltage being applied when a collision situation of any kind is recorded.

This is regularly the case with so-called rubber switches. The rubber switches have two different metal elements that are embedded in a rubber material and are usually wire-shaped, which are pushed against each other in the event of a collision so that the resistance achieved by the two metal elements changes. In the event of a connection of this type, the change in resistance on the side of the continuously rotatable component also effects a variation in the direct voltage value on the side of the rest of the body of the device, such that on the other side of the rotatable components it can be determined that a collision is taking place and/or has taken place, without a corresponding signal being necessary via a designated communication channel.

In another preferred embodiment the slip ring connection is also sufficient to inform the control system of an upcoming and/or ongoing collision situation, and the need for a separate cable for communication is obviated. According to this embodiment the apparatus for recording returns signals via the slip ring connection. In other words simple (temporally changeable) signals are impressed upon the direct voltage. In this way the direct voltage is modulated. On the sides of the rest of the body a suitable high-pass can filter out the direct voltage, and only the impressed signals are received. The control system can then prevent the movement of the rotatable component in the event of an upcoming or ongoing collision.

In both aspects of the invention the inventive idea can be employed especially advantageously if the medical diagnosis and/or intervention device comprises an articulated robot. This can be the case for example in an x-ray imaging device, with the articulated robot holding and moving an x-ray C-arm with an x-ray radiation source and an x-ray detector.

BRIEF DESCRIPTION OF THE DRAWINGS

A preferred embodiment of the invention will now be described with reference to the drawing, with the one FIGURE showing part of a six-axis articulated robot with collision sensors.

DETAILED DESCRIPTION OF THE INVENTION

The present FIGURE accordingly shows part of a medical diagnosis and/or intervention device, namely an x-ray imaging device, in which a six-axis articulated robot holds and moves an x-ray C-arm. Of primary interest is a hand 10 of the six-axis articulated robot which is continuously rotatable opposite an arm 11 of the six-axis articulated robot, as indicated by the arrow 14. The six-axis articulated robot can perform complex movements in which the hand 10 can move to practically any desired locations within the range of the robot's installation zone. In the course of these movements the hand can collide with obstacles. The hand 10 is fitted with several collision sensors 12, 12'. The collision sensors 12, 12' are for example simple push buttons of various types. On account of the continuous rotatability of the hand 10 opposite the arm 11 as indicated by the arrow 14, the sensors 12, 12' cannot be connected by cables. The sensors 12, 12' obtain their voltage via a slip ring 16. The slip ring 16 is constructed like conventional slip rings and need not be described in more detail here. Cables that lead to the slip ring 16 from a voltage supply on the one hand and from the slip ring 16 to the sensors 12, 12' on the other hand are not shown in the FIGURE. The sensors 12, 12' are preferably connected in a so-called daisy chain arrangement. This means that there is a voltage input connection and a voltage output connection. For each of the sensors 12, 12' one tap is assigned on the power input connection and one tap is assigned on the power output connection, to which it is connected. Now that the voltage is supplied wirelessly, the need for cabling for communication in the collision sensors 12, 12' is also obviated. The sensors 12, 12' are designed to send signals by radio or infrared to a receiver 18 of a control unit 20, which control the movements of the robot. The signals to be sent by the sensors 12, 12' are by no means highly complex. It is simply a matter of indicating whether or not a collision could take place or is currently taking place. If an obstacle connects with a push button 12 or 12', the control system 20 senses this and stops the robot.

The invention claimed is:

1. A medical device, comprising:
a movable component;
a control unit that controls a movement of the movable component;
a plurality of sensors arranged on the movable component wherein each sensor:
generates a signal in response to a collision between the movable component and an obstacle, and
wirelessly sends the signal to the control unit; and
wherein a voltage is supplied to the each sensor without a cable,
wherein the voltage is supplied to the each sensor by a battery,
wherein the battery is charged by a dynamo,
wherein the dynamo is only arranged on the movable component,
wherein the each sensor wirelessly sends the signal to the control unit by acting on changes of the voltage applied on the each sensor when the collision occurs via a rubber switch,
wherein the rubber switch comprises two metal elements that are embedded in a rubber material and are pushed against each other when the collision occurs that changes a resistance achieved by the two metal elements and the voltage applied on the each sensor, and
wherein the plurality of sensors are connected in a daisy chain arrangement.

2. The medical device as claimed in claim 1, wherein the movable component is rotatable about an axis of rotation.

3. The medical device as claimed in claim 2, wherein the voltage is supplied to the each sensor via a slip ring arranged on the movable component.

4. The medical device as claimed in claim 2, wherein the voltage is supplied to the each sensor inductively upon rotation of the movable component.

5. The medical device as claimed in claim 1, wherein the collision is an ongoing or upcoming collision.

6. The medical device as claimed in claim 1, wherein the medical device is a medical diagnosis or intervention device.

7. The medical device as claimed in claim 1, wherein the medical device is an x-ray imaging device comprising an x-ray C-arm arranged on an articulated robot.

8. A medical device, comprising:
a movable component that is continuously rotatable opposite a rest of body of the medical device about an axis of rotation;
a plurality of sensors arranged on the movable component wherein each sensor generates a signal in response to a collision between the movable component and an obstacle; and
a slip ring arranged on an intersection between the rest of body of the medical device and the movable component that conducts a direct voltage to the each sensor,
wherein the each sensor impresses the signal upon the direct voltage when the collision occurs,
wherein the each sensor wirelessly sends the signal to a control unit by acting on changes of the direct voltage applied on the each sensor when the collision occurs via a rubber switch, and
wherein the rubber switch comprises two metal elements that are embedded in a rubber material and are pushed against each other when the collision occurs that changes a resistance achieved by the two metal elements and the direct voltage applied on the each sensor, and
wherein the plurality of sensors are connected in a daisy chain arrangement.

9. The medical device as claimed in claim 8, wherein the impressed signal is received by a control unit via the slip ring.

10. The medical device as claimed in claim 8, wherein only the impressed signal is received by the control unit by high-pass filtering out the voltage.

* * * * *